United States Patent [19]

Horvath

[11] Patent Number: 5,013,326
[45] Date of Patent: May 7, 1991

[54] ARTIFICIAL HAND

[75] Inventor: Eduard Horvath, Vienna, Austria

[73] Assignee: Otto Bock Orthopadische Industrie Besitz- und Verwaltungs-KG, Duderstadt, Fed. Rep. of Germany

[21] Appl. No.: 381,604

[22] Filed: Jul. 18, 1989

[30] Foreign Application Priority Data

Jul. 18, 1988 [AU] Australia ............................. 1841/88

[51] Int. Cl.⁵ ............................................... A61F 2/54
[52] U.S. Cl. ........................................ 623/64; 294/902; 623/57
[58] Field of Search ........................ 623/57, 61, 63, 64; 901/31, 38; 294/902, 19.1, 19.2, 19.3, 22, 23, 23.5, 24, 25, 26, 26.5, 27.1

[56] References Cited

U.S. PATENT DOCUMENTS 2,494,460  1/1950  Trautman .
2,629,107  2/1953  Becker .

FOREIGN PATENT DOCUMENTS 0170479   2/1986   European Pat. Off. ............... 414/4
02219478  4/1987   European Pat. Off. ............. 623/57
1122667   1/9162   Fed. Rep. of Germany ........ 623/64
0689671  10/1979   U.S.S.R. ................................ 623/64
580152    8/1946   United Kingdom .
608640    9/1948   United Kingdom .
862437    3/1961   United Kingdom .

Primary Examiner—Randall L. Green
Assistant Examiner—David H. Willse
Attorney, Agent, or Firm—Herbert Dubno; Ronald Lianides

[57] ABSTRACT

An artificial hand has its finger gripper swingable about an axis which includes an angle of 30° to 70° with a plane normal to axis of a prosthesis connector and its fingers inclined at an acute angle to the finger carrier to provide a more natural orientation of the hand for picking up objects at pick-up surfaces located above a support surface for the object.

12 Claims, 2 Drawing Sheets

ARTIFICIAL HAND

FIELD OF THE INVENTION

My present invention relates to an artificial hand and, more particularly, to an artificial hand having a gripper corresponding to a thumb and at least one other gripper member corresponding to another finger of the hand and in which at least one of the grippers is displaceable in a swingable manner toward and away from the other gripper so that objects can be engaged between the thumb and the fingers or fingers forming the other gripper.

BACKGROUND OF THE INVENTION

In artificial hands of the aforedescribed type, generally each gripper is swingable about an axis which extends transversely and usually perpendicularly, to the axis of the prosthesis connector, i.e. the threaded or bayonet fixture by which the artificial hand is fastened to the remainder of the prosthesis; hereinafter, this fixture, which has a defined axis, will be described as a connector.

As a consequence of this swingable movement of each gripper about a respective axis transverse to the axis of the connector, the gripper movement is a scissor or tongs action enabling the jaws to engage an object between them.

This construction has the disadvantage that it is difficult to grip objects which have gripping surfaces located relatively high above the surface upon which the object stands. This is because it is difficult to place the artificial hand in a gripping position without bending the arm at such an angle that the surface on which the object rests will interfere with engagement of the object between the thumb and gripping finger of the artificial hand. Furthermore, even if engagement of the object is not prevented, the required orientation of the arm for engagement with high gripping surfaces of an object standing on a table, for example, makes the gripping motion extremely awkward and difficult to carry out.

OBJECTS OF THE INVENTION

It is the principal object of the present invention to provide an artificial hand which obviates the aforementioned disadvantages and can be used with greater facility, especially for gripping objects at locations spaced well above the surface upon which the objects are supported.

Another object of this invention is to provide an improved artificial hand which affords a more natural gripping action.

SUMMARY OF THE INVENTION

These objects are attained, in accordance with the invention, in that the gripper formed with the finger other than the thumb and preferably with both an index finger and a middle finger, has a finger carrier with which the index finger and middle finger form acute angles while the thumb includes also an acute angle with the thumb carrier, and wherein the pivot axis of the swingable carrier, i.e. the finger carrier and/or the thumb carrier, forms an acute angle with a plane normal to the axis of the prosthesis connector, and further in that the drive for approximating the fingers and the thumb and spreading them apart is located in the finger carrier and/or the thumb carrier which can be configured as a sleeve or hollow housing to receive the drive.

More specifically, the artificial hand of the invention can comprise:

a connector having a first axis and formed with means for connecting the artificial hand to a prosthesis;

a thumb carrier mounted on the connector and formed with a thumb of the artificial hand and constituting a first gripper;

a finger carrier mounted on the connector and formed with at least one finger of the artificial hand extending at an acute angle to the finger carrier and constituting a second gripper opposed to the first gripper, the grippers being relatively swingable on the connector toward and away from one another;

means for mounting at least one of the grippers for swinging movement relative to the connector about a second axis which forms an acute angle with a plane normal to the axis of the connector and opening toward the the connector; and a drive for relatively swinging the grippers and rotating the one of the grippers about the second axis.

The drive, as noted, is received in at least one of the finger and thumb carriers which can be formed with a sleeve portion receiving the drive. The drive can be a planetary gear transmission having two electric motor inputs as described in U.S. Pat. No. 4,923,477.

The angle included by the second axis with the plane normal to the axis of the connector and opening toward the connector is between 30° and 70°.

With this configuration, the natural gripping movement of a hand for engagement with an object to lift it from a surface is applied to the object well above the axis of the connector and by pivot motion about least one axis inclined thereto so that the arm can have a more natural positioning for this engagement. If the finger carrier and/or the thumb carrier is hollow or shell like, the drive can be built into the shell or sleeve, thereby minimizing the spacing required for the drive and allowing a more compact construction as well as a more esthetically satisfying artificial hand from the cosmetic point of view.

An inclination of the second axis to the normal plane of 30° to 70° has been found to correspond to a positioning of the artificial hand very similar to that of a natural hand in gripping objects located above a support surface.

According to a feature of the invention, the pivot bearing of the finger carrier can be arranged on an arm which is connected with a prosthesis connector. The gripper formed with the index finger and middle finger then can move with a kinematic gripping action which approximates that of the fingers of the natural hand.

In an especially preferred feature of the invention, the arm provided with the pivot bearing of the finger carrier can be swingably connected with the prosthesis connector at a pivot axis which is parallel to the pivot axis of the finger carrier and preferably coincides with a pivot axis of the gripper provided with the thumb. This kinematic action has been found to reduce distortion and the danger of damage to the cosmetic glove which is customarily provided for the artificial hand.

If a mutual movement of the grippers toward and away from one another is desired, the pivot axis of the arm should coincide with the pivot axis of the thumb gripper. For an especially effective mutual displacement of the grippers without damage or distortion to the cosmetic glove, the finger carrier can be connected via a link with the prosthesis connector and preferably with the bearing carrier thereof to form a four-point linkage which permits controlled movement of the finger carrier about the arm pivotally connected to the prosthesis connector.

Of course, simpler embodiments can be provided if desired. For example, the arm forming the pivot bearing for the finger carrier can be rigidly connected to the prosthesis connector and the thumb gripper can be held rigidly on the prosthesis connector in addition or as an alternative. Of course, the finger carrier can be fixed to the prosthesis connector if the thumb carrier and its gripper is swingably journaled. In all of the embodiments described, objects resting upon a surface can be engaged by the movement of at least one gripper toward the other and this action takes place whether or not the other gripper is simultaneously moved toward the first. However, since distortion of the cosmetic glove may result, the preferred or best mode embodiment of the invention is for the two grippers to be moved toward and away from one another.

BRIEF DESCRIPTION OF THE DRAWING

The above and other objects, features and advantages of my invention will become more readily apparent from the following description, reference being made to the accompanying highly diagrammatic drawings in which.

SPECIFIC DESCRIPTION

Figure 1:
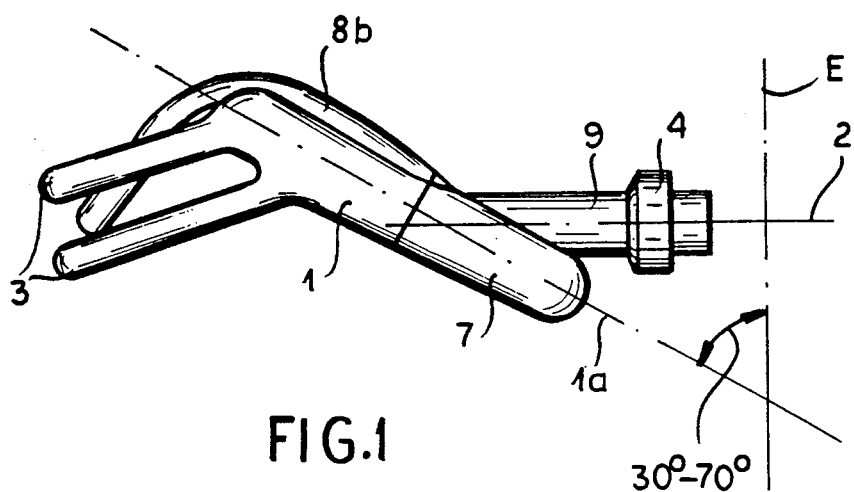
FIG. 1 is a side elevational view in highly diagrammatic form of a first embodiment of an artificial hand according to the invention.

A finger carrier 1 has fingers 3 extending at an acute angle thereto and corresponding generally to the index finger and the middle finger of a natural hand. The finger carrier is rotatably journaled on a swingable arm 7 which extends laterally from a bearing carrier 9 of a prosthesis connector 4 which may be threaded to allow attachment to an arm prosthesis.

The pivot axis 1a of the finger carrier 1 includes an angle of about 30° to 70° to a plane E which is normal or perpendicular to the axis 2 of the prosthesis connector and opens in the direction of the connector 4. This angle disposes the fingers in a relatively natural position with respect to the axis of a wrist, for example, as is the case with a natural hand attempting to pick up an object standing on a surface.

The laterally projecting arm 7, swingable on the bearing carrier 9, has a pivot axis 8a formed by a pin 8 which lies parallel to the axis 1a which is swingable thereabout.

This pin 8 extends forwardly to form a thumb gripper 8b from which the thumb also extends at an acute angle to the axis 8a.

Figure 3:
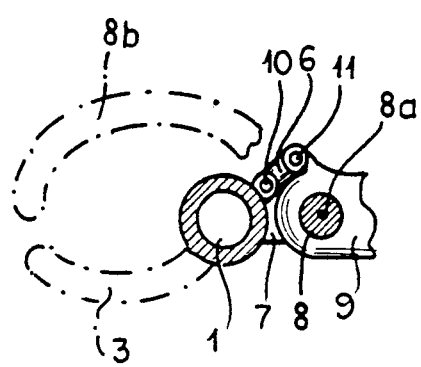
FIG. 3 is a section taken generally transverse to the axes of the embodiment of FIG. 2 facing rearwardly, showing in dot-dash lines the thumb and fingers of the grippers which are located forwardly of the section and thus are not visible in solid lines in FIG. 3.

As can be seen from FIG. 3, the finger carrier 1 and the bearing carrier 9 have lateral projections or lugs 10 and 11 in which a link 6 is articulated at each of its ends. The link 6 forms with the remaining parts, a four-point linkage of which the laterally projecting arm 7 constitutes one crank, the finger carrier 1 constitutes a coupler, the prosthesis connector 4 the frame and the link 6 the second crank.

The drive for the movement of the gripper is provided in the finger carrier 1 and the laterally projecting arm 7. The drive has been shown in diagrammatic form at D as fully housed in a sleeve formed by the finger carrier 1. This drive can be a planetary gear drive energized by two electric motors as described in the aforementioned copending application.

A similar drive can be provided in the thumb gripper 8.

Upon energization of the drive or drives, the finger carrier 1 can be rotated relative to the lateral arm 7 and swinging motion imparted with the link 6 to the carrier 1 and arm 7, which rotates the gripper 8b so that the latter is swung in the bearing carrier 9. The paths of the two swinging movements are shown in dot-dash lines in FIG. 4 and thus the swinging path of the thumb gripper 8b corresponds to the path 5a and the swinging path of the finger gripper 3 to the dot-dash path 5b.

Figure 5:
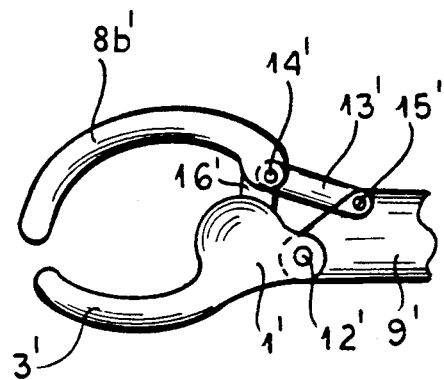
FIG. 5 is a view of a second embodiment of the artificial hand in highly diagrammatic form to show the kinematics involved and viewed along the axis of the finger carrier.

In the embodiment of FIG. 5, the finger carrier 1 is journaled directly on the bearing carrier 9' via the pivot bearing 12'. The thumb 8b' is connected via a bell crank or angle lever 16 ' with the drive which can be located within the finger carrier 1' and thus can thereby form a counterbearing for the drive of the finger carrier.

A link 13' is pivotally connected to the bell crank lever 16' at 14' and the other end of the link 13' is pivotally connected at 15 to the bearing carrier. Here again a four-point linkage is provided whereby the finger carrier 1' with its lug part projecting toward the bearing 12' forms the frame, the region of the bearing carrier 9' between points 12' and 15' forms one crank, the level 16' forms the other crank and the link 13' forms the coupler.

In this case, the drive can impart a counterclockwise rotation to the finger carrier 1' which will result in a clockwise swing of the gripper 8b' via the lever 16' and a movement of the finger carrier 1' about pivot point 12' and a movement of the bell crank lever 16' about pivot point 14'.

The pivot point 14' then swings freely about the point 15' of the coupler 13'. As a consequence, the grippers 3' and 8b' open. For closure of the hand, the finger carrier 1' is moved in the opposite sense, i.e. in the clockwise sense so that the bell crank lever 16' and the gripper 8b' will swing in the counterclockwise sense and close the grippers.

To simplify the construction, one of the two grippers can be fixed while the other, either the gripper 8b or the gripper 3, approaches the stationary gripper part. In that case, the movable part need only be displaced over half of the path 5a or 5b.

Figure 2:
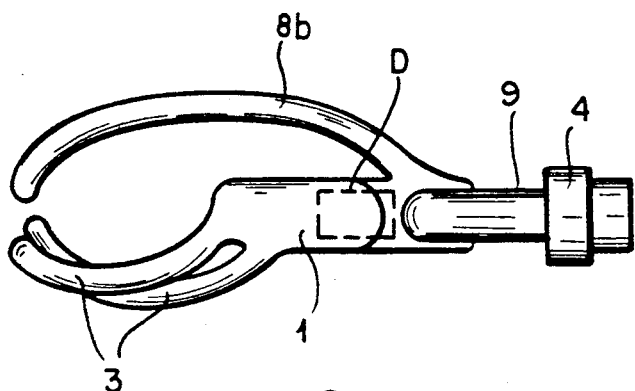
FIG. 2 is a plan view thereof.
Figure 4:
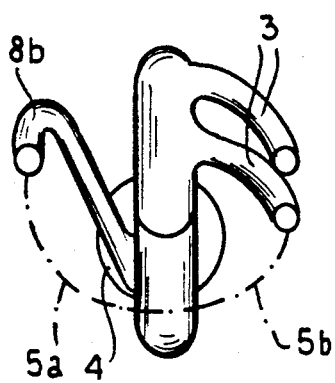
FIG. 4 is a perspective view of the artificial hand from the front.
Figure 6:
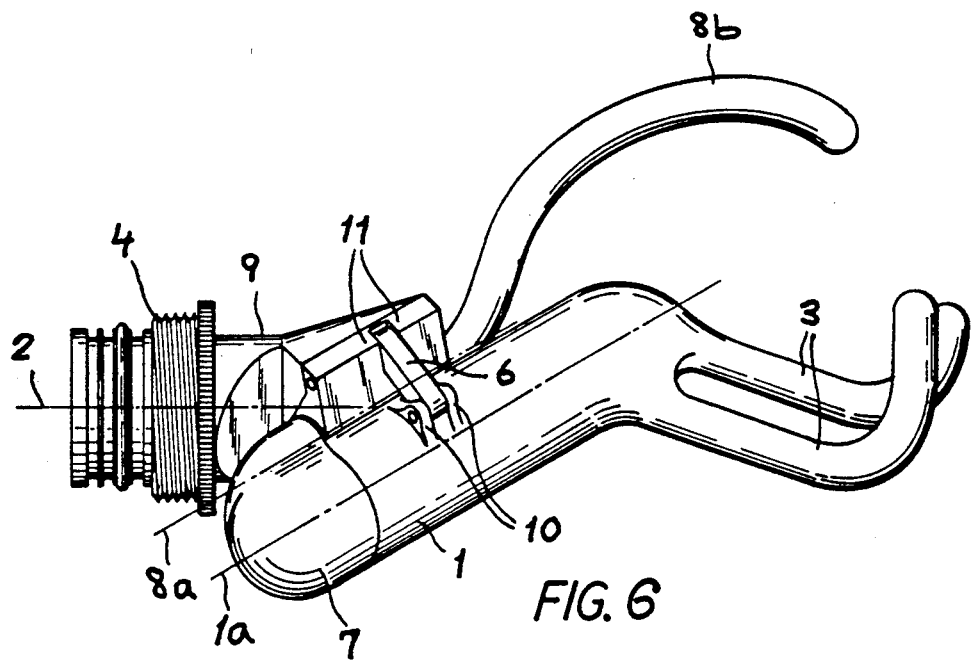
FIG. 6 is a perspective view illustrating the hands of FIGS. 1, 2 and 4 in greater detail.
Figure 7:
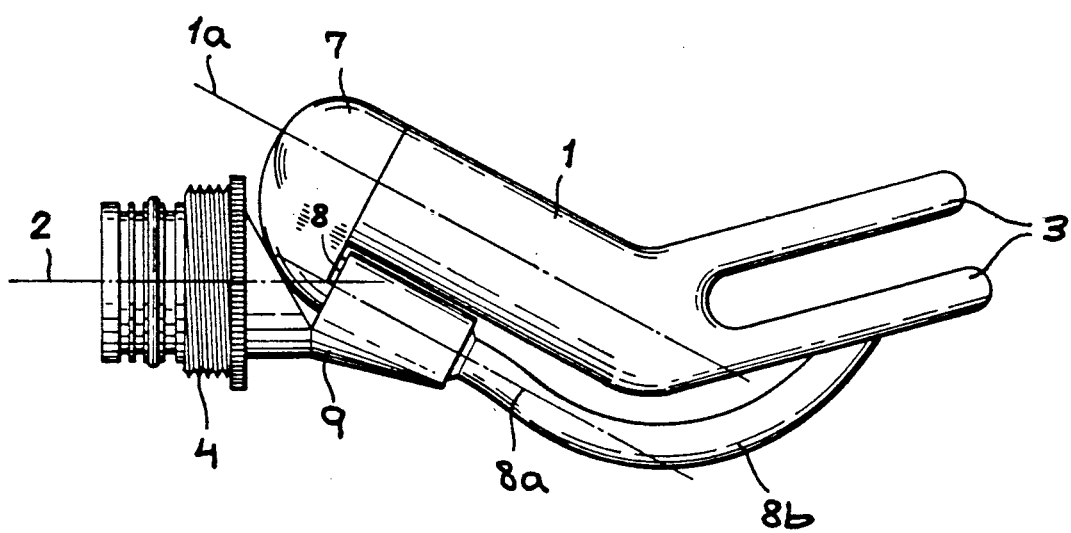
FIG. 7 is a perspective view of the hand of FIG. 6 rotated 120° about the axis of the threaded prosthesis connector thereof.

FIGS. 6 and 7 are perspective views showing in greater detail the application of the kinematics of FIG. 3 to the embodiment of FIGS. 1, 2 and 4.

It will be apparent from FIGS. 6 and 7 that member 7 is pivotal in the bearing holder 9 about the axis 8a which corresponds to the pivot axis of the thumb 8b and is parallel to the pivot axis 1a of the part 1 carrying the fingers 3 on the member 7. Both of these axes are superimposed in the illustration of FIG. 1 because of the angle in which the view in that figure is taken and both extend at the aforementioned angle of 30°-70° to the plane E perpendicular to the axis 2 of the connector 4 retaining the hand on the prosthesis.

FIG. 6 also illustrates more clearly how the link 6 interconnects the parts 1 and 9.

I claim:

1. An artificial hand, comprising:
    a connector having a first axis and formed with means for connecting the artificial hand to a prosthesis;
    a thumb carrier formed with a thumb of the artificial hand, extending at an acute angle to said thumb carrier, and constituting a first gripper;
    a finger carrier formed with at least one finger of the artificial hand extending at an acute angle to a longitudinal axis of said finger carrier and constituting a second gripper opposed to the first gripper, said grippers being relatively swingable toward and away from one another around a common second axis connecting said carriers of said grippers and including an acute angle with a plane normal to said first axis of said connector, and opening toward said connector;
    means for mounting one of said grippers to said connector; and
    a drive for swinging at least one of said grippers about said common second axis.

2. The artificial hand defined in claim 1 wherein said drive is received in at least one of said finger and thumb carriers.

3. The artificial hand defined in claim 2 wherein said at least one of said finger and thumb carriers is formed with a sleeve portion receiving said drive.

4. The artificial hand defined in claim 3 wherein said angle included by said second axis with said plane normal to said first axis of said connector and opening toward said connector is between 30° and 70°.

5. The artificial hand defined in claim 4 wherein said means for mounting at least one of said grippers for swinging movement relative to said connector about said second axis includes an arm projecting laterally from said connector and forming a pivot bearing for said finger carrier, whereby said finger carrier is swingable about said second axis.

6. An artificial hand, comprising:
    a connector having a first axis and formed with means for connecting the artificial hand to a prosthesis;
    a thumb carrier mounted on said connector and formed with a thumb of the artificial hand and constituting a first gripper;
    a finger carrier mounted on said connector and formed with at least one finger of the artificial hand extending at an acute angle to a longitudinal axis of said finger carrier and constituting a second gripper opposed to the first gripper, said grippers being relatively swingable on said connector toward and away from one another;
    means for mounting at least one of said grippers for swinging movement relative to said connector about a second axis which forms an acute angle with a plane normal to said first axis of said connector and opening toward said connector;
    a drive for relatively swinging said grippers and rotating said one of said grippers about said second axis, said drive being received in at least one of said finger and thumb carriers being formed with a sleeve portion receiving said drive, said angle included by said second axis with said plane normal to said first axis of said connector and opening toward said connector being between 30° and 70°, said means for mounting at least one of said grippers for swinging movement relative to said connector about said second axis including an arm projecting laterally from said connector and forming a pivot bearing for said finger carrier whereby said finger carrier is swingable about said second axis; and means for swingably mounting said arm on said connector about a third axis on a bearing carrier of said connector, said third axis being parallel to said second axis.

7. The artificial hand defined in claim 6 wherein said thumb carrier is swingable on said connector about said third axis.

8. The artificial hand defined in claim 6, further comprising a link pivotally connected to said finger carrier and connecting said finger carrier to said connector.

9. The artificial hand defined in claim 8 wherein said link is also pivotally connected to said bearing carrier.

10. The artificial hand defined in claim 5 wherein said arm is rigidly connected to said connector.

11. The artificial hand defined in claim lo wherein said thumb carrier is rigidly connected to said connector.

12. The artificial hand defined in claim 4 wherein said finger carrier is rigidly connected to said connector and said thumb carrier is swingably mounted on said connector.

* * * * *